(12) United States Patent
Leyden et al.

(10) Patent No.: US 7,155,838 B2
(45) Date of Patent: Jan. 2, 2007

(54) APPARATUS FOR GAUGING A DIMENSION OF AN OBJECT

(75) Inventors: Roger Leyden, Willow Springs, IL (US); Dennis Hayes, Chicago, IL (US)

(73) Assignee: Se-Kure Controls, Inc., Franklin Park, IL (US)

( * ) Notice: Subject to any disclaimer, the term of this patent is extended or adjusted under 35 U.S.C. 154(b) by 0 days.

(21) Appl. No.: 10/806,919

(22) Filed: Mar. 23, 2004

(65) Prior Publication Data
US 2005/0210694 A1    Sep. 29, 2005

(51) Int. Cl.
*G01B 3/02* (2006.01)
*A47G 1/00* (2006.01)
*G09F 19/16* (2006.01)

(52) U.S. Cl. .............................. 33/492; 33/493; 33/512

(58) Field of Classification Search .......... 33/492–494, 33/483–484, 832, 512, 833; 40/360, 626, 40/628, 630, 219, 900; D10/71, 70; 428/204, 428/912.2; D6/303–307
See application file for complete search history.

(56) References Cited

U.S. PATENT DOCUMENTS

| | | | | |
|---|---|---|---|---|
| D24,404 S | * | 6/1895 | Wiederer | D6/305 |
| 558,014 A | * | 4/1896 | Elborne | 356/397 |
| 865,709 A | * | 9/1907 | Johnson | 356/397 |
| D56,025 S | * | 8/1920 | Nowacki | D6/306 |
| 1,457,964 A | * | 6/1923 | Harry | 33/512 |
| D67,630 S | * | 6/1925 | Trippi | D6/306 |
| D67,633 S | * | 6/1925 | Trippi | D6/306 |
| 1,953,796 A | * | 4/1934 | Crocker | 428/624 |
| 2,036,021 A | * | 3/1936 | Dexter | 430/320 |
| 2,145,732 A | * | 1/1939 | Nickle | 427/166 |
| D116,049 S | * | 8/1939 | Noth | D10/71 |
| 2,270,069 A | * | 1/1942 | Martin | 33/512 |
| 2,324,334 A | * | 7/1943 | Sutton | 33/512 |

(Continued)

OTHER PUBLICATIONS

Busy Kids'website for childfurniture/mirrors.html titled "MIRRORS" dated Jun. 21, 2003 as printed from the Internet Archive Wayback Machine on Jun. 8, 2006, all pages and in particular the T-Rex Mirror p. 3, the Bear Wall Mirror p. 4, and the Measure Me Mirror p. 6.*

(Continued)

*Primary Examiner*—R. Alexander Smith
(74) *Attorney, Agent, or Firm*—Wood, Phillips, Katz, Clark & Mortimer (57) ABSTRACT

An apparatus for gauging the dimension of an object. The apparatus has a wall with a generally flat front surface, facing a first direction, and a peripheral edge. Space graduations are provided on the wall relative to which a dimension of an object placed in front of the wall can be gauged. The surface on the wall reflects an image of an object located in front of the wall. At least one of i) a depiction of at least one of a) an animate object; b) an inanimate object; and c) a scene; ii) at least one word; iii) a design; and iv) a logo is provided on the wall and is viewable from in front of the wall in conjunction with the spaced graduations and a reflected image from the surface on the wall. The wall is formed so that the shape of at least a portion of the peripheral edge is at least nominally matched in shape to a shape of at least a portion of the at least one of i) a depiction of at least one of a) an animate object; b) an inanimate object; and c) a scene; ii) at least one word; iii) a design; and iv) and a logo.

25 Claims, 5 Drawing Sheets

U.S. PATENT DOCUMENTS

| | | | | |
|---|---|---|---|---|
| 2,369,988 | A | * | 2/1945 | Steckler .................... 434/187 |
| D167,945 | S | * | 10/1952 | Larson ........................ D10/71 |
| 2,736,100 | A | * | 2/1956 | Landau ........................ 33/512 |
| 2,791,417 | A | * | 5/1957 | Daroff ......................... 369/22 |
| D187,493 | S | * | 3/1960 | Zuckerman .................. D10/71 |
| 2,932,897 | A | * | 4/1960 | Huber ......................... 33/758 |
| D190,525 | S | * | 6/1961 | Stroyman .................... D10/71 |
| 3,775,153 | A | * | 11/1973 | Greenberg et al. .......... 428/204 |
| D257,962 | S | * | 1/1981 | Youdelman et al. ......... D10/71 |
| D277,720 | S | * | 2/1985 | Leifert ........................ D6/306 |
| D277,833 | S | * | 3/1985 | Bergstedt ..................... D10/71 |
| D295,150 | S | * | 4/1988 | Farrell ......................... D10/71 |
| 4,842,921 | A | * | 6/1989 | Sorko-Ram ................. 428/187 |
| 4,851,061 | A | * | 7/1989 | Sorkoram ..................... 156/63 |
| D312,217 | S | * | 11/1990 | Kang ........................... D10/70 |
| 5,013,592 | A | * | 5/1991 | Culpepper ................... 428/46 |
| 5,128,194 | A | * | 7/1992 | Sorko-Ram ................. 428/172 |
| D378,992 | S | * | 4/1997 | Dachille ...................... D10/70 |
| 5,702,649 | A | * | 12/1997 | Taylor ......................... 264/1.9 |
| D396,195 | S | * | 7/1998 | Morrow ....................... D10/70 |
| D396,422 | S | * | 7/1998 | Dietterich et al. ........... D10/62 |
| D403,514 | S | * | 1/1999 | Beaumont .................... D6/305 |
| D406,539 | S | * | 3/1999 | O'Neil ........................ D10/71 |
| D419,080 | S | * | 1/2000 | Panek ......................... D10/70 |
| D460,366 | S | * | 7/2002 | Winter ........................ D10/70 |
| 6,845,580 | B1 | * | 1/2005 | Noble ......................... 40/582 |

OTHER PUBLICATIONS

Busy Kids' website titled "Friendly T-Rex Mirror" dated Aug. 15, 2003 as printed from the Internet Archive Wayback Machine on Jun. 8, 2006, p. 1.*

Busy Kids' website titled "Bear Wall Mirror" dated Jul. 2, 2003 as printed from the Internet Archive Wayback Machine on Jun. 8, 2006, p. 1.*

Busy Kids' website titled "Measure Me Mirror" dated Feb. 28, 2003 as printed from the Internet Archive Wayback Machine on Jun. 8, 2006, p. 1.*

Watch Me Grow Up website for childrens growth charts dated Dec. 24, 2003 as printed from the Internet Archive Wayback Machine on Jun. 8, 2006, all 7 page and in particular the mirrors shown on p. 3 along with the other animal based charts shown throughout.*

* cited by examiner

APPARATUS FOR GAUGING A DIMENSION OF AN OBJECT

BACKGROUND OF THE INVENTION

1. Field of the Invention

This invention relates to an apparatus for gauging a dimension of an object and, more particularly, to an apparatus in front of which an individual can position him-/herself to gauge a body dimension.

2. Background Art

Parents commonly take an interest in monitoring the changing height of their young boy or girl. Height scales are commonly provided in homes and in commercial establishments on walls, door frames, and other independent structures for this purpose. In their simplest forms, these height scales consist of an array of spaced graduations with height dimensions numerically identified in proximity thereto. These height scales are typically used by having the child back against the surface upon which the graduations are located. The height of the child is determined by identifying the particular graduation at which the top of the child's head aligns. The child is generally advised of his or her height which may be committed to memory. Alternatively, markings may be placed on the wall, or other structure, in the vicinity of the graduations, to identify the height of a particular child. Obviously, this latter practice is practical only if the height scale is provided in the user's own space.

In another form, a flexible sheet with graduations on a front surface thereof is utilized. The sheet may be rolled into a compact state for storage, when not in use.

Parents commonly do wish to have their children develop an awareness of their bodily growth. While monitoring using a basic height scale allows a parent to convey growth information to their child, this type of presentation is generally made in such a purely mechanical fashion that the information may not be intriguing to the child and consequently may not be retained.

To make the child's growth more interesting to him/her, it is known to adorn the region in the vicinity of the height scale with information, designs, or scenes that peak the interest of the child. This may generate more interest on the part of the child, in the process of regularly monitoring his/her height, as a consequence of which there may be greater awareness on the part of the child of his/her development.

Another dimension that has been added to the basic height scale is the inclusion of a mirror. The child is given additional incentive to use the height scale by reason of having the ability to see his/her reflected image in relationship to the graduations. This allows the child to see his/her height dimension in a more meaningful manner.

A common construction of these height measuring mirrors utilizes a rectangular piece of mirrored glass with the length dimension aligned vertically. The glass may be framed, as by a piece of wood, or the like, to contribute to its aesthetics. The framed mirror may be leaned against a wall, or other vertical structure, to support the same in a useable state. To avoid tipping of the framed mirror, the mirror is leaned against the wall or other structure at an angle to vertical. As a result, the measurements taken from the mirror may not be accurate. This arrangement also potentially results in an unsightly structure and one that is fairly obtrusive and prone to being inadvertently run into and/or tipped.

Alternatively, the framed mirror can be mounted from a vertically extending surface in the same manner as a framed picture is mounted. By reason of the potential weight of the framed mirror, fairly substantial mounting fasteners may be required.

With glass mirrors, it is common to apply adornment, as through painting, on the forwardmost, exposed surface of the glass. As such, the adornment is prone to being nicked or scratched and otherwise has a tendency to get an altered appearance over time. Eventually, the adorned mirror may become unsightly.

Another drawback with glass mirrors is that they are prone to breaking into a potentially dangerous form. A user could be injured under the weight of the mirror, as it tips, and/or by sharp edges resulting from broken pieces of the mirror.

The industry continues to seek out a design for a height scale that can be purchased economically, yet that will be aesthetically pleasing, convenient to use, and fully functional. At the same time, it is desirable to have all of the above attributes for the totality of the desired life of the height measurement structure, which typically may be from five to ten years.

SUMMARY OF THE INVENTION

In one form, the invention is directed to an apparatus for gauging the dimension of an object. The apparatus has a wall with a generally flat front surface, facing a first direction, and a peripheral edge. Space graduations are provided on the wall relative to which a dimension of an object placed in front of the wall can be gauged. The surface on the wall reflects an image of an object located in front of the wall. At least one of i) a depiction of at least one of a) an animate object; b) an inanimate object; and c) a scene; ii) at least one word; iii) a design; and iv) a logo is provided on the wall and is viewable from in front of the wall in conjunction with the spaced graduations and a reflected image from the surface on the wall. The wall is formed so that the shape of at least a portion of the peripheral edge is at least nominally matched in shape to a shape of at least a portion of the at least one of i) a depiction of at least one of a) an animate object; b) an inanimate object; and c) a scene; ii) at least one word; iii) a design; and iv) and a logo.

In one form, the wall has a length extending in a vertical direction and a width. The graduations allow gauging of the height of an object located in front of the wall.

The length of the wall may be substantially greater than the width of the wall.

In one form, the wall has a first layer with a front and rear and at least a portion of the at least one of i) a depiction of at least one of a) an animate object; b) an inanimate object; and c) a scene; ii) at least one word; iii) a design; and iv) a logo is applied to the rear of the layer and is viewable through the first layer at the front of the first layer.

In one form, the first layer is a clear plastic material.

The first layer may have a thickness between the front and rear of the first layer that is in the range of 0.04 to 0.12 inches.

The rear of the first layer may be coated with a first material that is viewable through the first layer and reflects an image of an object located in front of the first layer.

The first material may be aluminum or other metal material.

The metal material may be applied in a vacuum chamber.

In one form, the wall has a second layer applied at the rear of the first layer so that the first material and the at least one of i) a depiction of at least one of a) an animate object; b)

an inanimate object; and c) a scene; ii) at least one word; iii) a design; and iv) a logo resides between the first and second layers.

In one form, the second layer has a front and rear and a thickness between the front and rear of the second layer is in the range 0.04 and 0.12 inches.

In one form, the second layer is made from High Impact Polystyrene.

In one form, the second layer is secured to the first layer through a pressure sensitive adhesive.

The portion of the peripheral edge may be formed through laser cutting.

In one form, the apparatus has a front and rear with a thickness between the front and rear. The apparatus has an areal extent and a substantially uniform thickness over substantially the entire areal extent of the apparatus.

In one form, the portion of the peripheral edge is non-straight.

In one form, the wall has a height and a width and first and second space sides spaced in a widthwide direction. The portion of the peripheral edge on the first spaced side of the wall has a non-straight configuration over more than one half the height of the wall at the first spaced side.

In one form, the wall has a nominally squared shape with four transverse edge portions. One of the transverse edge portions has a first length and a running length of the one transverse edge portion is substantially greater than the first length.

In one form, the portion of the peripheral edge has adjacent contiguous portions which extend along first and second transverse lines, with the first and second lines defining an acute angle.

In one form, there is at least one opening through the wall. The opening is fully surrounded and capable of receiving a fastener to facilitate mounting of the wall to a support.

The invention is further directed to an apparatus for gauging a dimension of an object and having a wall with a generally flat front surface facing in a first direction and a peripheral edge. Spaced graduations are provided on the wall relative to which a dimension of an object placed in front of the wall can be gauged. A surface on the wall reflects an image of an object located in front of the wall. At least one of i) a depiction of at least one of a) an animate object; b) an inanimate object; and c) a scene; ii) at least one word; iii) a design; and iv) a logo are provided on the wall and viewable from in front of the wall in conjunction with the spaced graduations and a reflective image from the surface on the wall. The wall has a first layer and a second layer. The first layer defines the flat front surface. The at least one of i) a depiction of at least one of a) an animate object; b) an inanimate object; and c) a scene; ii) at least one word; iii) a design; and iv) a logo is located between the first and second layers so as to be viewable from in front of the wall through the first layer.

In one form, a reflective coating is applied to the second layer over the at least one of i) a depiction of at least one of a) an animate object; b) an inanimate object; and c) a scene; ii) at least one word; iii) a design; and iv) a logo to allow an image of an object located in front of the wall to be viewable through the first layer.

The invention is further directed to a method of forming an apparatus for gauging a dimension of an object. The method includes the steps of: providing a first layer with a front and rear; forming at least one of i) a depiction of at least one of a) an animate object; b) an inanimate object; and c) a scene; ii) at least one word; iii) a design; and iv) a logo on the rear of the first layer so that the at least one of i) a depiction of at least one of a) an animate object; b) an inanimate object; and c) a scene; ii) at least one word; iii) a design; and iv) a logo is viewable through the first layer at the front of the first layer; coating the rear of the first layer with a first material that is viewable through the first layer and capable of reflecting an image of an object located in front of the first layer; providing graduations on the first layer relative to which a dimension of an object placed in front of the first layer can be gauged; and cutting the first layer to define a peripheral edge, so that the shape of at least a portion of the peripheral edge is at least nominally matched in shape to a shape of at least a portion of the at least one of i) a depiction of at least one of a) an animate object; b) an inanimate object; and c) a scene; ii) at least one word; iii) a design; and iv) a logo.

The method may further include the step of applying a second layer over the first layer. The step of cutting may involve cutting the first and second layers simultaneously.

The step of applying the second layer may involve bonding the second layer to the first layer through a pressure sensitive adhesive.

The step of coating the first layer may involve vacuum coating the rear of the first layer with a first material that is made from metal.

The step of simultaneously cutting the first and second layers may involve simultaneously laser cutting the first and second layers.

In one form, the step of coating the rear of the first layer may involve coating the rear of the first layer over the at least one of i) a depiction of at least one of a) an animate object; b) an inanimate object; and c) a scene; ii) at least one word; iii) a design; and iv) a logo.

DETAILED DESCRIPTION OF THE DRAWINGS

Figure 1:
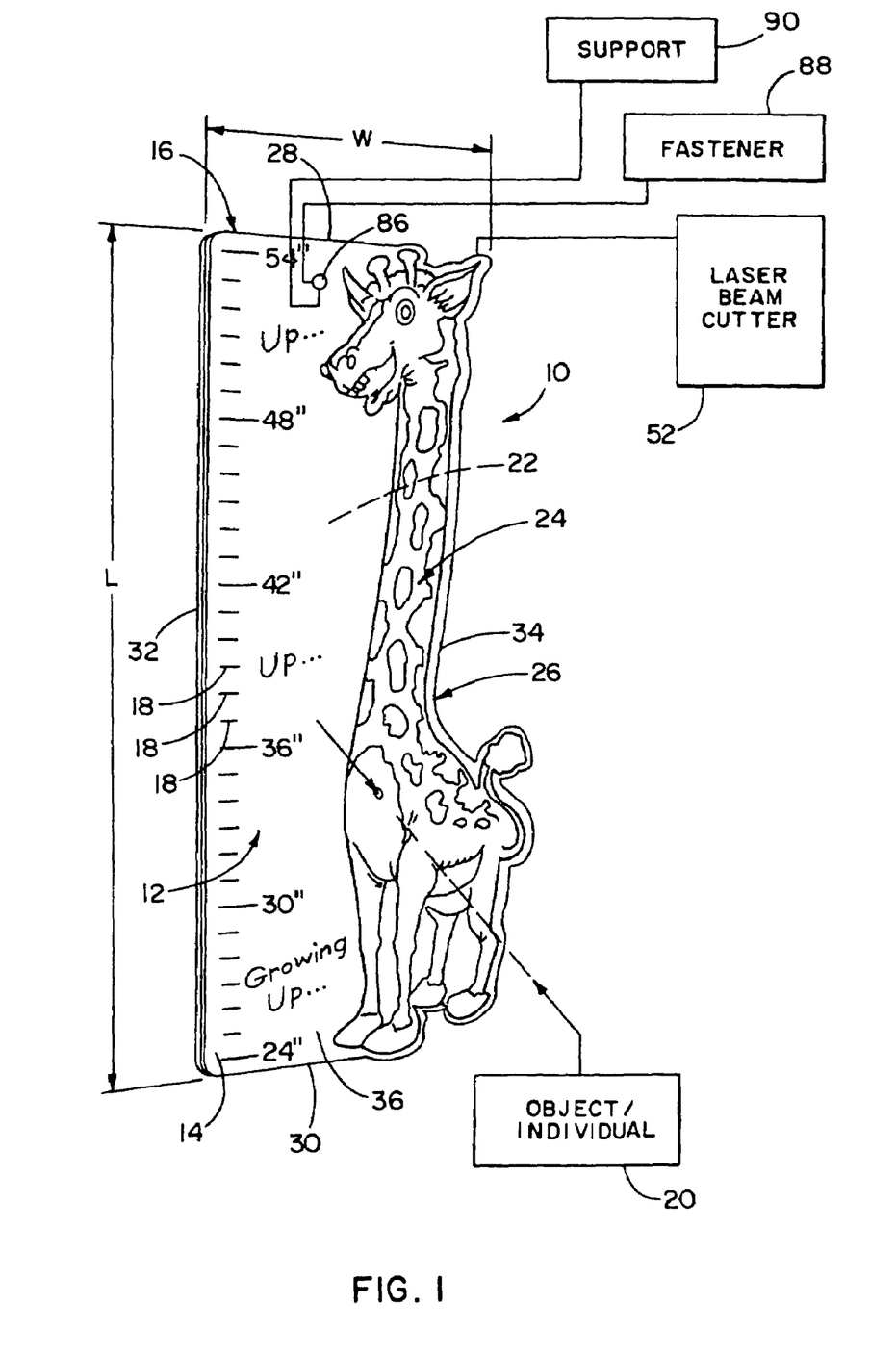
FIG. 1 is a partially schematic, front, perspective view of one form of apparatus for gauging a dimension of an object, according to the present invention.
Figures 2, 4:
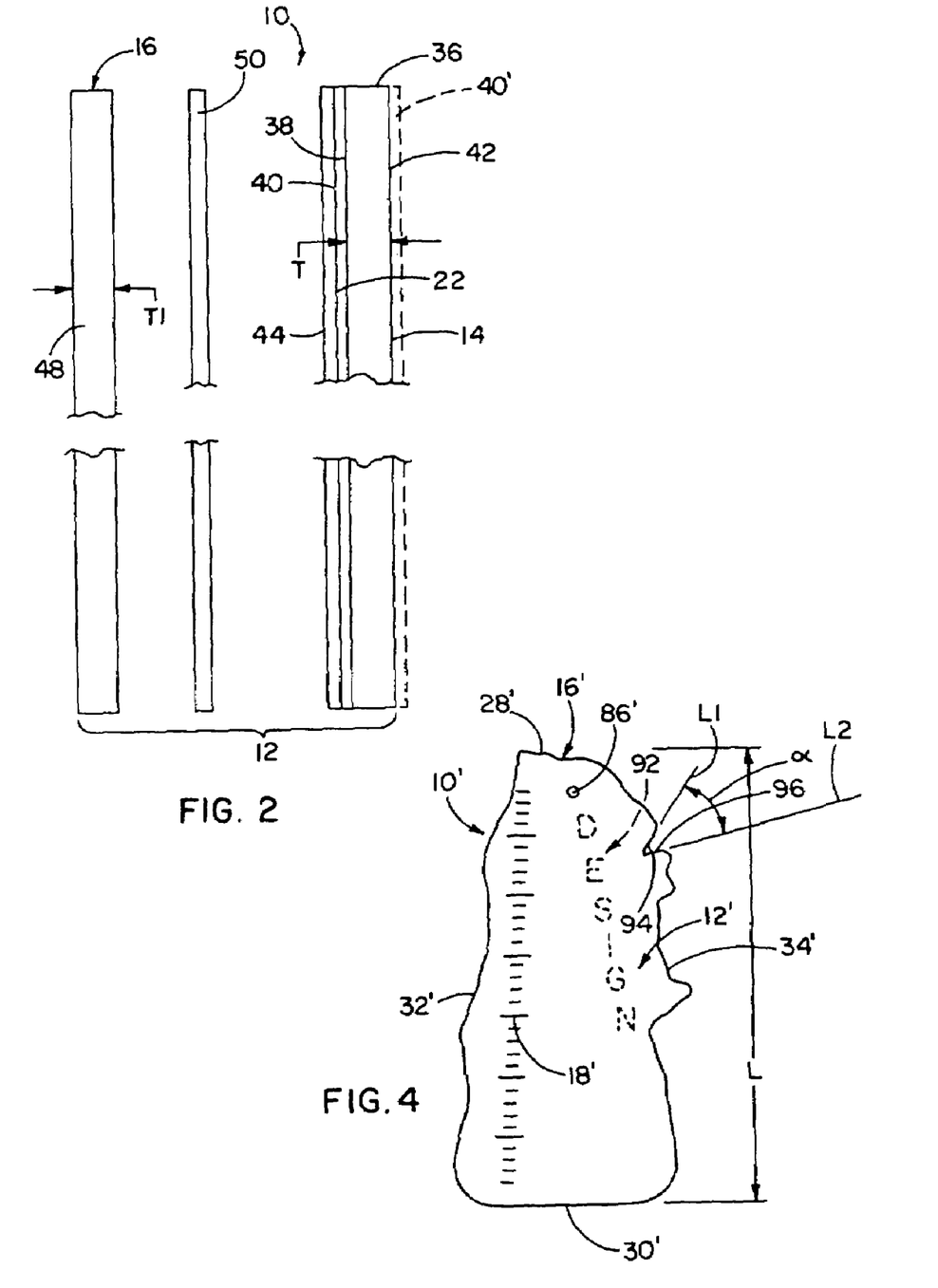
FIG. 2 is an enlarged, fragmentary, exploded, side elevation view of a wall on the inventive apparatus of FIG. 1.
FIG. 4 is a front elevation view of a modified form of apparatus for gauging a dimension of an object, according to the present invention, and including a generic design thereon.

In FIGS. 1 and 2, one form of apparatus for gauging a dimension of an object, according to the present invention, is shown at 10. The apparatus 10 consists of a wall at 12 having a generally flat, front surface 14 facing in a first direction. The wall 12 has a surrounding, peripheral edge 16. Spaced graduations 18 are provided on the wall 12 relative to which a dimension of an object/individual 20, placed in front of the wall 12, can be gauged. A surface 22 on the wall 12 reflects an image of the object/individual 20 located in front of the wall 12. A design 24, in this embodiment in the form of a depiction of a giraffe, is provided on the wall 12 and is viewable from in front of the wall 12 in conjunction with both the graduations 18 and a reflected image from the surface 22 of the object/individual 20 situated in front of the wall 12. The wall 12 is formed so that at least a portion at 26 of the peripheral edge 16 is at least nominally matched in shape to the shape of part of the subject matter of the design 24, in this case the depiction of the giraffe. In this embodiment, the edge portion 26 conforms nominally to the shape of part of the head, neck, torso, legs, and tail of the giraffe.

In this embodiment, the wall 12 has a length dimension L extending in a vertical direction, and a width dimension W transversely thereto. The length dimension L is substantially greater than the width dimension W. The wall 12 has a generally squared/rectangular shape with top and bottom edge portions 28, 30 and side edge portions 32, 34, spaced in a widthwise direction. The entire vertical dimension of the side edge portion 34, and part of each of the top and bottom edge portions 28, 30, have a non-straight shape that nominally conforms to the shape of the design/giraffe.

The wall 12 consists of a first, primary layer 36 having a thickness T between the front and rear thereof. The thickness T, in one preferred form, is on the order of 0.08 inches. Preferably, the thickness T is in the range of 0.04 to 0.12 inches.

The design/depiction of the giraffe is applied to the rear surface 38 of the first layer 36 by any suitable means. In one form, the design is applied in reverse-image form through a decal, paint, screen printing, or by any other means known to those skilled in the art, as a separate layer 40 on the rear surface 38 of the first layer 36. Alternatively, the design can be formed integrally with the layer 36, at the rear thereof. The invention also contemplates that the design 24 could be applied as an optional layer 40' at the front surface 42 of the layer 36, by integral formation on the front surface 42, or by integration thereof between the front and rear surfaces 42, 38.

In one preferred form, the first layer 36 is defined by a clear plastic material so that the design/depiction of the giraffe is viewable through the first layer 36 at the front thereof.

A reflective coating 44 is applied at the rear of the layer 36. The coating 44 defines the forwardly facing surface 22 that reflects the image of the object/individual 20 at the front of the wall 12. The material for the coating 44 may be aluminum, or another metal or another reflective material. The reflection of the image of the object/individual 20 can be seen through the thickness of the first layer 36. Preferably, the coating 44 is applied in a vacuum chamber over the surface 38. The design layer 40 can be masked or, alternatively, the reflective coating 44 can be applied over the entire area of the rear surface 38 of the layer 36, including that to which the layer 40 is applied.

A second, primary layer 48 is applied to the rear of the first layer 36 through a pressure sensitive adhesive layer 50. The second layer 48 has a thickness T1 between its front and rear. The thickness T1 is, in one form, on the order of 0.08 inches. The thickness T1 may be in the range of 0.04 to 0.12 inches. The second layer 38 may be made from a High Impact Polystyrene. The layer 48 is laminated to a desired thickness with a hair-cell finish.

Once the layers 36, 48 are united through the pressure sensitive adhesive layer 50, the peripheral edge 16 is cut to the desired shape, preferably through a laser beam cutter at 52. The entire peripheral edge 16 can be formed through the laser beam cutter 52 or, alternatively, the laser beam cutter 52 can be used to cut only the contoured, non-straight portions of the peripheral edge 16. The straight portions of the peripheral edge 16 can be cut using conventional saws. The layers 36, 48 can be preformed in blanks matching the desired end configuration for the wall 12, with the exception of that portion of the peripheral edge 16 that must be more intricately cut, as through the use of the laser beam cutter 52.

Figure 3:
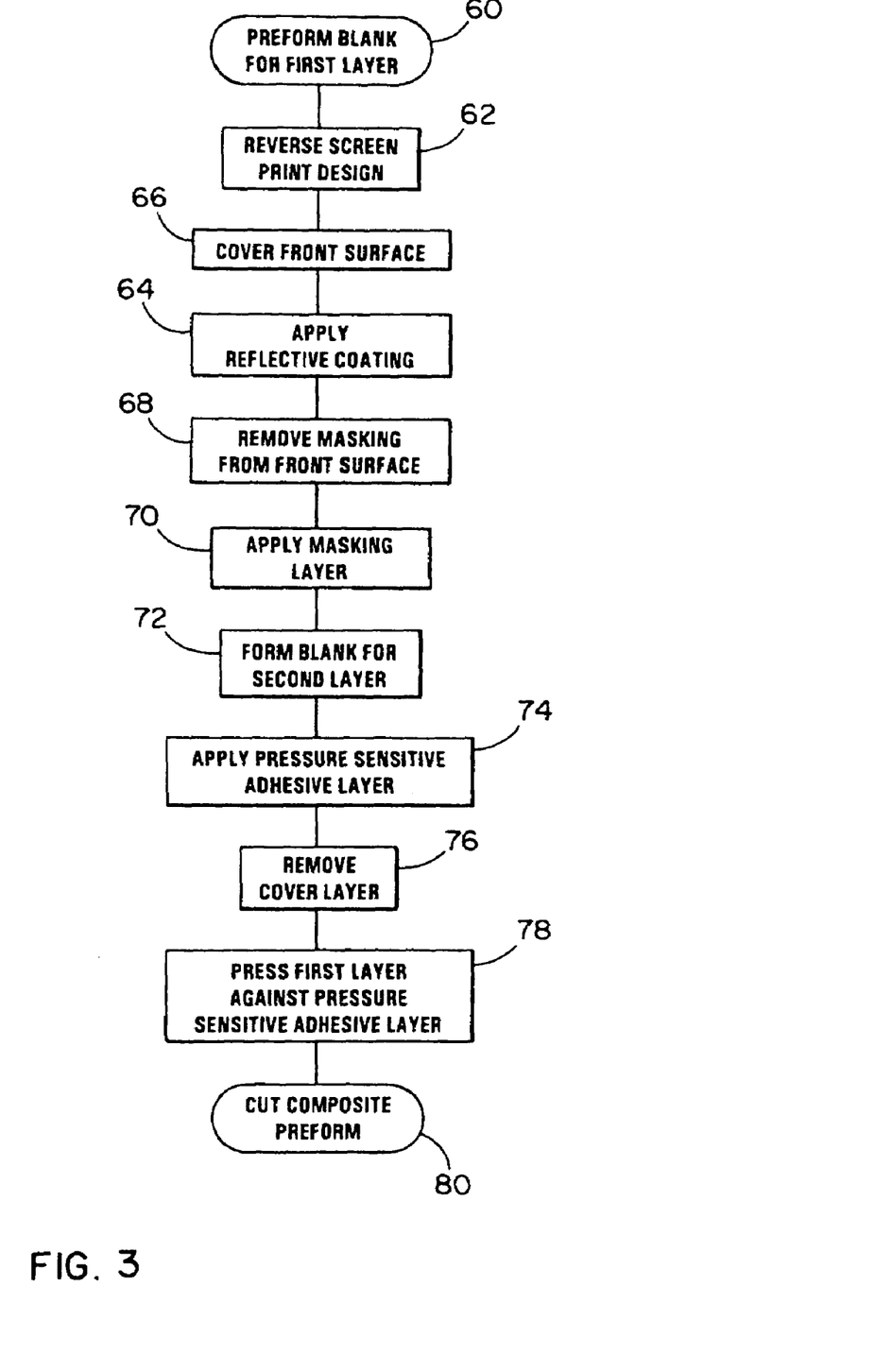
FIG. 3 is a flow diagram showing a method of making the inventive apparatus.

One process for forming the inventive apparatus 10 will be described with respect to FIG. 3, taken in conjunction with FIGS. 1 and 2. Initially, a blank for the first layer is preformed, as from a 4 foot by 8 foot sheet of plastic material of the desired thickness, as shown at block 60 FIG. 3. A "design" 24, as described in greater detail below, and shown in FIG. 1 as a depiction of a giraffe, is then reverse-image applied, as by screen printing, on the rear surface 38 of the first layer 36, as shown at block 62. The reflective coating 44 is then applied, as in a vacuum chamber, as shown at block 64, either over part or all of the design, or over the rear surface 38 of the first layer 36 with the design masked.

Preparatory to the application of the reflective coating 44, an optional step of masking/covering the front surface 14 of the first layer 36 may be carried out, as shown at block 66. This covering step may involve applying a poly-masking material, as conventionally used for this purpose. If the cover step is performed, at the completion of the application of the reflective coating 44, the masking from the front surface is removed, as shown at block 68. A new masking layer is applied to the front surface of the first layer 36, as shown at block 70. A blank, for defining the second layer 48, is then formed, as shown at block 72. The pressure sensitive adhesive layer 50 is then applied to the second layer 48, as shown at block 74. A cover layer, on the exposed portion of the pressure sensitive adhesive layer 50, is then removed, as shown at block 76. The first layer is then pressed against the pressure sensitive adhesive layer to unite the first and second layers 36, 48, as shown at block 78, to produce a composite preform, as shown at block 78. The composite preform is then cut to produce the desired end shape for the apparatus, as shown at block 80. The graduations 18 can be applied at the same time that the reverse image of the design 24 is applied. Alternatively, the graduations 18 can be applied to the front surface 42 of the first layer 36 or otherwise integrated into the wall 12.

The second layer 48 functions as a stiffening element and also protects the layer 40, through which the design is applied to the first layer 36 and the second coating 44, to avoid damage thereto.

One or more openings 86 can be provided partially or fully through the wall 12 to accept a fastener 88 that can be directed into a support 90 for the apparatus 10 to maintain the apparatus 10 in an operative state in which meaningful dimensional gauging can be carried out.

In the embodiment shown, the wall 12 has a substantially uniform thickness over the full areal extent of the wall 12. This allows the apparatus 10 to be mounted upon a vertically extending surface with a relatively insignificant projection therefrom. The apparatus 10 is not obtrusive in nature yet affords an aesthetically pleasing construction that, in this form, if not abused, will maintain its high quality appearance for its useful life.

While FIG. 1 depicts one potential design arrangement, as shown in FIG. 4, the contemplated graphics and designs are virtually unlimited. FIG. 4 depicts, at 10', another form of apparatus for gauging the dimensions of an object, according to the invention. The apparatus 10' has a wall 12' having the same makeup of elements as described for the wall 12 on the apparatus 10, including graduations 18'. The adornment of the wall 12', corresponding to the design 24, is shown generically as a "design" at 92, which design is at least one of i) a depiction of at least one of a) an animate object; b) an inanimate object; and c) a scene; ii) at least one word; iii) a design; and iv) a logo. The design 92 can be merely decorative or may be, and is preferably, a subject matter associated with the concept of growth. The design 92 could be customized to a particular user. In any event, it is desirable that the design 92 be somehow attractive to a young boy or girl and that it be viewable in conjunction with the reflected image of the boy/girl situated in front of the wall 12'.

The apparatus 10' has an irregular peripheral edge 16' with a top edge portion 28' and side edge portions 32', 34'. In this case, the bottom edge portion 30' is straight to allow the apparatus 10' to be supported, if desired, in an operative position upon a flat underlying surface. An opening 86' is provided through the wall 12' to facilitate its mounting, as upon a flat upwardly projecting surface.

In this embodiment, the design 92 to which the exemplary side edge portion 34' nominally conforms, has a running length that is substantially greater than the vertical dimension L on the side edge portion 84'. The running length is the actual distance traveled following the edge portion 34' over the dimension L. The edge portion 34' nominally conforms to at least a portion of the design 92. The side edge portion 34' follows a meandering route, causing portions thereof to be oriented generally along different lines which change directions such that adjacent portions define an acute angle between lines approximating the projecting direction thereof. More specifically, as one example, an edge portion 94 projects in a direction approximated by the line L1, whereas an adjacent edge portion 96 projects in a direction approximated by the line L2. The angle a between the lines L1 and L2 of projection of the adjacent, contiguous portions 94, 96 is less than 90 degrees, i.e. acute.

The other edge portions 28', 32' can be defined by straight and or non-straight lengths. To enhance the appearance of the apparatus 10', it may be desirable to have the non-straight pattern at the edge portion 34' extend over at least one half, and more preferably, the full height thereof. In other designs, as set out below, this is not a desirable feature.

Figure 5:
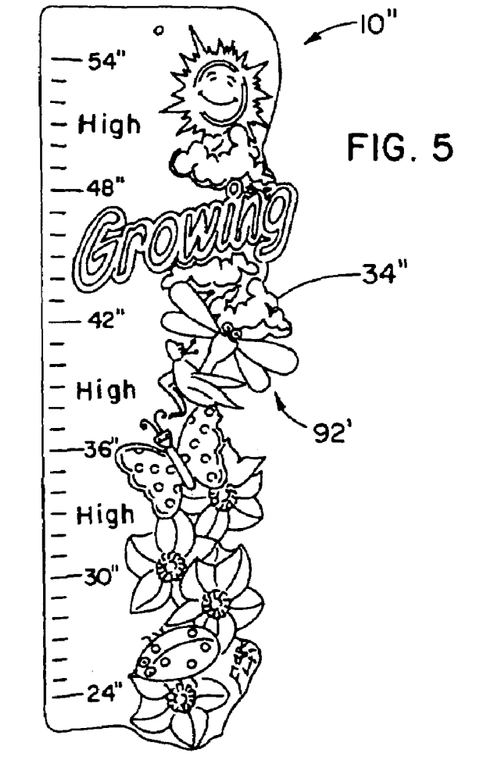
FIG. 5 is a front elevation view of a further modified form of apparatus, according to the present invention.

In FIG. 5, another form of apparatus, according to the present invention, is shown at 10". The apparatus 10" is shown with an alternative design 92' consisting of flowers, insects, clouds, etc., portions of which the side edge portion 34" nominally conforms to over substantially the entire height thereof.

Figure 6:
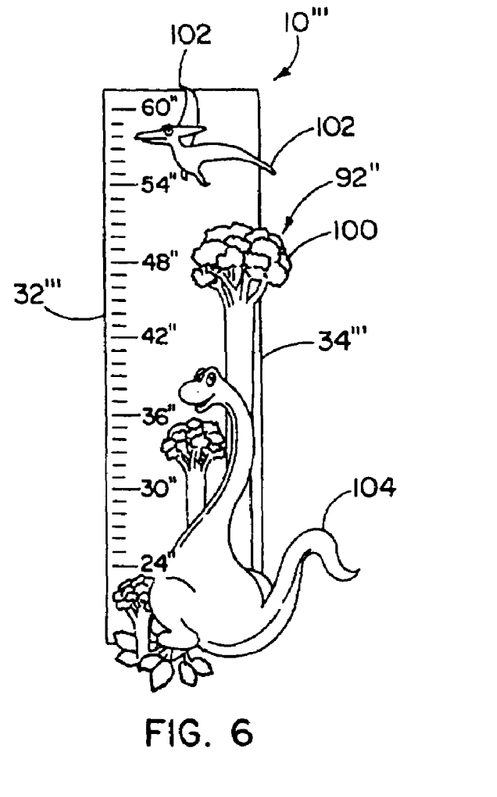
FIG. 6 is a front elevation view of a further modified form of apparatus, according to the present invention.

In FIG. 6, a further modified form of apparatus is shown at 10''' with the design 92" being a dinosaur theme. The side edge portion 34''' is substantially straight and parallel to the opposite side edge portion 32'''. The design juts out and deviates from a linear path at discrete locations and nominally conforms to vegetation at 100, and wings 102 and a tail 104 of prehistoric subjects, shown as part of the design 92".

Figure 7:
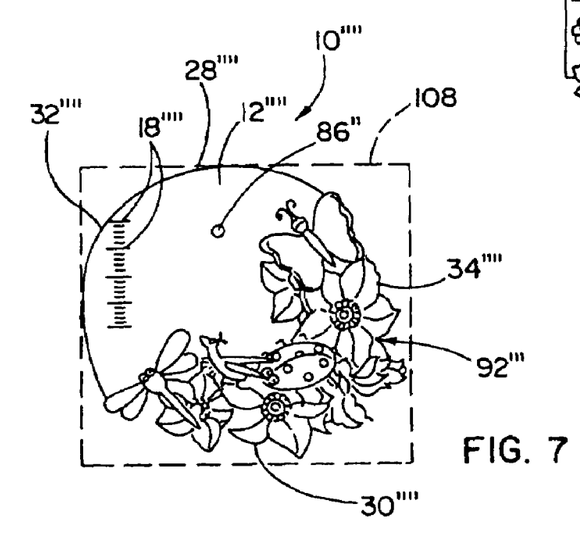
FIG. 7 is a front elevation view of a still further modified form of apparatus, according to the present invention.

In FIG. 7, a still further modified form of apparatus, according to the present invention, is shown at 10''''. The wall 12'''' on the apparatus 10'''' has a generally rounded shape and may be hung by extending a fastener through an opening 86'' therein to support the apparatus 10'''' in an elevated position to effectively gauge a dimension of the object/individual 20 in front thereof. The wall 12'''' may be mounted so that the graduations 18'''' may be located at a level appropriate to the height of the subject boy/girl. The perimeter of the wall 12'''' is generally approximated by a squared shape, as indicated by the dotted lines 108. In this case, the vertical dimension of the squared shape is less than the horizontal dimension. Corresponding top and side edge portions 28'''', 32'''' have a curved shape, rather than the straight, orthogonal relationship as shown in the prior embodiments. The bottom and side edge portions 30'''' and 34'''' are nominally matched to a part of the adjacent portion of the design 92''' on the wall 12'''.

Figure 8:
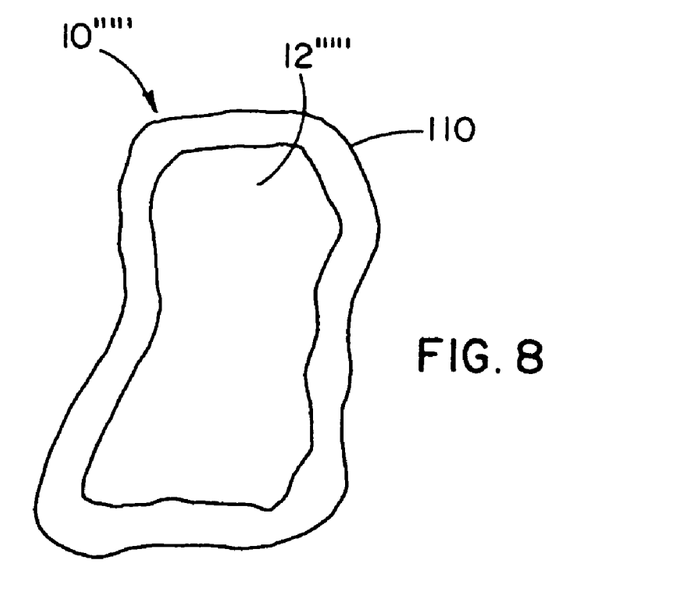
FIG. 8 is a front elevation view of another form of apparatus, according to the present invention, and including a peripheral frame.

In a further variation, as shown in FIG. 8, an apparatus $10^{\prime x5}$, according to the present invention, has an irregularly shaped wall $12^{\prime x5}$ with a surrounding frame 110 that can be formed around the wall $12^{\prime x5}$. While the invention contemplates that a frame 110 can be used, preferably, the "sculpting" of the peripheral edges of the walls, as described above, creates a decorative pattern that obviates the need for a frame to contribute to the aesthetics of the apparatus.

Figure 9:
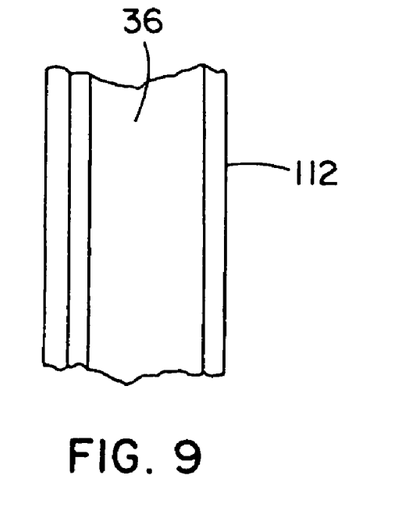
FIG. 9 is an enlarged, fragmentary, side elevation view of layer on the inventive apparatus with a protective coating on a surface thereof.

Other modifications are contemplated, according to the present invention. As just examples, as shown in FIG. 9, a hard coat layer 112 can be applied to the layer 36 to enhance its durability and resistance to scratching.

The apparatus 10, 10', 10'', 10''', 10'''', $10^{\prime x5}$ could be integrated into another structure to enhance its appearance and/or utility.

The foregoing disclosure of specific embodiments is intended to be illustrative of the broad concepts comprehended by the invention.

The invention claimed is:

1. An apparatus for gauging a dimension of an object, the apparatus comprising:
   a wall having a generally flat front surface facing in a first direction and a peripheral edge;
   spaced graduations on the wall relative to which a dimension of an object placed in front of the wall can be gauged;
   a surface on the wall which reflects an image of an object located in front of the wall; and
   a depiction of at least one of a) an animate object; b) an inanimate object; and c) a scene, in addition to the graduations, and viewable from in front of the wall in conjunction with the spaced graduations and a reflective image from the surface on the wall,
   wherein the front surface has a first area and the depiction of at least one of a) an animate object; b) an inanimate object; and c) a scene occupies only a part of the first area and a user can see his/her reflected image in a portion of the first area not occupied by the depiction of at least one of a) an animate object; b) an inanimate object; and c) a scene, in such a manner that the reflected image appears to the user to be integrated with the subject matter of the depiction of at least one of a) an animate object; b) an inanimate object; and c) a scene.

2. The apparatus for gauging the dimension of an object according to claim 1 wherein the wall has a length extending in a vertical direction and a width and the graduations allow gauging of the height of an object located in front of the wall.

3. The apparatus for gauging the dimension of an object according to claim 2 wherein the length of the wall is substantially greater than the width of the wall.

4. The apparatus for gauging the dimension of an object according to claim 1 wherein the wall comprises a first layer having a front and rear and at least a portion of the depiction of at least one of a) an animate object; b) an inanimate object; and c) a scene is applied to the rear of the first layer and viewable through the first layer at the front of the first layer.

5. The apparatus for gauging the dimension of an object according to claim 4 wherein the first layer comprises a clear plastic material.

6. The apparatus for gauging the dimension of an object according to claim 5 wherein the first layer has a thickness between the front and rear of the first layer that is in the range of 0.04–0.12 inches.

7. The apparatus for gauging the dimension of an object according to claim 4 wherein the rear of the first layer is coated with a first material that is viewable through the first layer and reflects an image of an object located in front of the first layer.

8. The apparatus for gauging the dimension of an object according to claim 7 wherein the first material comprises aluminum.

9. The apparatus for gauging the dimension of an object according to claim 7 wherein the first material comprises a metal material that is applied in a vacuum chamber.

10. The apparatus for gauging the dimension of an object according to claim 7 wherein the wall comprises a second layer applied at the rear of the first layer so that the first material and the depiction of at least one of a) an animate object; b) an inanimate object; and c) a scene resides between the first and second layers.

11. The apparatus for gauging the dimension of an object according to claim 10 wherein the second layer has a front and rear and a thickness between the front and rear of the second layer that is in the range of 0.04–0.12 inches.

12. The apparatus for gauging the dimension of an object according to claim 10 wherein the second layer comprises High Impact Polystyrene.

13. The apparatus for gauging the dimension of an object according to claim 10 wherein the second layer is secured to the first layer through a pressure sensitive adhesive.

14. The apparatus for gauging the dimension of an object according to claim 10 wherein a reflective coating is applied to the first layer over the depiction of at least one of a) an animate object; b) an inanimate object; and c) a scene to allow an image of an object located in front of the wall to be viewable through the first layer.

15. The apparatus for gauging the dimension of an object according to claim 1 wherein the portion of the peripheral edge is formed through laser cutting.

16. The apparatus for gauging the dimension of an object according to claim 1 wherein the apparatus has a front and rear with a thickness between the front and rear of the apparatus and an areal extent and the apparatus has a substantially uniform thickness over substantially the entire areal extent of the apparatus.

17. The apparatus for gauging the dimension of an object according to claim 1 wherein the portion of the peripheral edge is non-straight.

18. The apparatus for gauging the dimension of an object according to claim 1 wherein the wall has a height and a width and first and second sides spaced in a widthwise direction and the portion for the peripheral edge on the first spaced side of the wall has a non-straight configuration over more than one-half the height of the wall at the first spaced side.

19. The apparatus for gauging the dimension of an object according to claim 1 wherein the wall has a nominally squared shape with four transverse edge portions and one of the transverse edge portions has a first length and a running length of the one transverse edge portion is substantially greater than the first length.

20. The apparatus for gauging the dimension of an object according to claim 1 wherein the at least portion of the peripheral edge has adjacent contiguous portions which extend generally along first and second transverse lines, the first and second lines defining an acute angle.

21. The apparatus for gauging the dimension of an object according to claim 1 wherein there is at least one opening through the wall, the opening fully surrounded and capable of receiving a fastener to facilitate mounting of the wall to a support.

22. The apparatus for gauging a dimension of an object according to claim 1 wherein the wall is formed so that the shape of at least a portion of the peripheral edge is at least nominally matched in shape to a shape of at least a portion of the depiction of at least one of a) an animate object; b) an inanimate object; and c) a scene.

23. The apparatus for gauging a dimension of an object according to claim 1 wherein the graduations are located at the portion of the first area not occupied by the depiction of at least one of a) an animate object; b) an inanimate object; and c) a scene.

24. The apparatus for gauging a dimension of an object according to claim 1 wherein the depiction of at least one of a) an animate object; b) an inanimate object; and c) a scene comprises an animal so that the user has a perception from the front of the apparatus that he/she is standing next to the animal.

25. The apparatus for gauging a dimension of an object according to claim 1 wherein the depiction of at least one of a) an animate object; b) an inanimate object; and c) a scene is at an edge of the portion of the first area so that the depiction of at least one of a) an animate object; b) an inanimate object; and c) a scene frames/edges the portion of the first area.

* * * * *